(12) United States Patent
Arcand (10) Patent No.: US 7,896,642 B2
(45) Date of Patent: Mar. 1, 2011

(54) BALLOON FOLDING DEVICE

(75) Inventor: Benjamin Arcand, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 863 days.

(21) Appl. No.: 11/498,520

(22) Filed: Aug. 3, 2006

(65) Prior Publication Data
US 2008/0048363 A1 Feb. 28, 2008

(51) Int. Cl.
B29C 59/02 (2006.01)

(52) U.S. Cl. .................. 425/393; 425/409; 425/450.1

(58) Field of Classification Search ............... 425/343, 425/392–393, 409, 450.1
See application file for complete search history.

(56) References Cited

U.S. PATENT DOCUMENTS

| | | | | |
|---|---|---|---|---|
| 3,344,475 A * | 10/1967 | Gioe | | 425/330 |
| 3,372,435 A * | 3/1968 | Ford | | 425/392 |
| 3,502,767 A * | 3/1970 | Morrison et al. | | 425/351 |
| 4,509,909 A * | 4/1985 | Arends | | 425/388 |
| 4,519,766 A * | 5/1985 | Spengler | | 425/302.1 |
| 5,147,302 A | 9/1992 | Euteneuer et al. | | 604/103 |
| 5,209,799 A | 5/1993 | Vigil | | 156/156 |
| 5,336,234 A | 8/1994 | Vigil et al. | | 606/159 |
| 5,342,307 A | 8/1994 | Euteneuer et al. | | 604/103 |
| 5,350,361 A | 9/1994 | Tsukashima et al. | | |
| 5,571,540 A * | 11/1996 | Weyenberg et al. | | 425/343 |
| 5,681,522 A | 10/1997 | Roychowdhury | | 264/532 |
| 5,759,172 A | 6/1998 | Weber et al. | | 604/96 |
| 5,783,227 A * | 7/1998 | Dunham | | 425/318 |
| 5,792,415 A | 8/1998 | Hijlkema | | 264/530 |
| 6,296,655 B1 | 10/2001 | Gaudoin et al. | | 606/194 |
| 6,325,826 B1 | 12/2001 | Vardi et al. | | 623/1.35 |
| 6,425,882 B1 | 7/2002 | Vigil | | 604/99.01 |
| 6,623,451 B2 | 9/2003 | Vigil | | 604/99.01 |
| 6,770,092 B2 | 8/2004 | Richter | | 623/1.35 |
| 6,988,881 B2 | 1/2006 | Motsenbocker et al. | | 425/392 |
| 2003/0083687 A1 | 5/2003 | Pallazza | | 606/191 |
| 2004/0026825 A1* | 2/2004 | Bergsma et al. | | 425/393 |
| 2005/0060027 A1 | 3/2005 | Khenansho et al. | | 623/1.35 |
| 2006/0091585 A1 | 5/2006 | Kelley | | 264/239 |

FOREIGN PATENT DOCUMENTS

EP 0202649 11/1986

OTHER PUBLICATIONS

U.S. Appl. No. 11/138,202, filed May 26, 2005, Meyer et al.
U.S. Appl. No. 11/138,196, filed May 26, 2005, Gregorich et al.
U.S. Appl. No. 11/138,022, filed May 26, 2005, Gregorich et al.
U.S. Appl. No. 11/417,466, filed May 4, 2006, Hegg.

* cited by examiner

Primary Examiner—Richard Crispino
Assistant Examiner—Thu Khanh T Nguyen
(74) Attorney, Agent, or Firm—Vidas, Arrett & Steinkraus, P.A.

(57) ABSTRACT

A balloon folding device comprises a first die having an external contacting surface and a second die having a cavity. A portion of the cavity comprises a contacting surface shaped complimentary to the external contacting surface of the first die. The second die is movable with respect to the first die. A balloon catheter having a primary balloon and a secondary balloon is oriented with the secondary balloon located between the first die and the second die. The secondary balloon is folded by moving the second die toward the first die until the contacting surfaces of the dies contact, fold and deflate the secondary balloon. In some embodiments, the dies are moved until at least a portion of the external contacting surface of the first die is oriented within the cavity of the second die.

20 Claims, 6 Drawing Sheets

BALLOON FOLDING DEVICE

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

In some embodiments this invention relates to implantable medical devices, their manufacture, and methods of use. Some embodiments are directed to delivery systems, such as catheter systems of all types, which are utilized in the delivery of such devices. Some embodiments are directed to the manufacture and preparation of said delivery systems.

2. Description of the Related Art

Within the vasculature, it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels.

Balloon catheters intended for use at vessel bifurcations often have auxiliary portions, such as an auxiliary inflation balloon. Such balloon catheters are used to deliver and expand specialized stents that have dedicated side branch structures, wherein the auxiliary portions are used to achieve proper expansion of the side branch structure.

Auxiliary portions add bulk to a delivery system and increase the unexpanded profile, thus affecting flexibility and deliverability of the system. There remains a need for specialized preparation of suitable delivery systems in order to provide a compact, low profile delivery device.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, the invention is directed to a balloon folding device comprising a first die having an external contacting surface and a second die having a cavity. A portion of the cavity comprises a contacting surface. The second die is movable with respect to the first die. During movement, the external contacting surface of the first die moves within the cavity of the second die as the balloon is folded.

In some embodiments, the balloon folding device folds the balloon to impart a crescent shape.

In at least one embodiment, the invention is directed to a method of folding a secondary balloon. A balloon folding device is provided, the device comprising a first die having a contacting surface and a second die having a cavity that includes a contacting surface. A secondary balloon is oriented between the dies of the balloon folding device, and the balloon is folded by moving the second die with respect to the first die.

These and other embodiments which characterize the invention are pointed out with particularity in the claims annexed hereto and forming a part hereof.

However, for further understanding of the invention, its advantages and objectives obtained by its use, reference can be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 1:
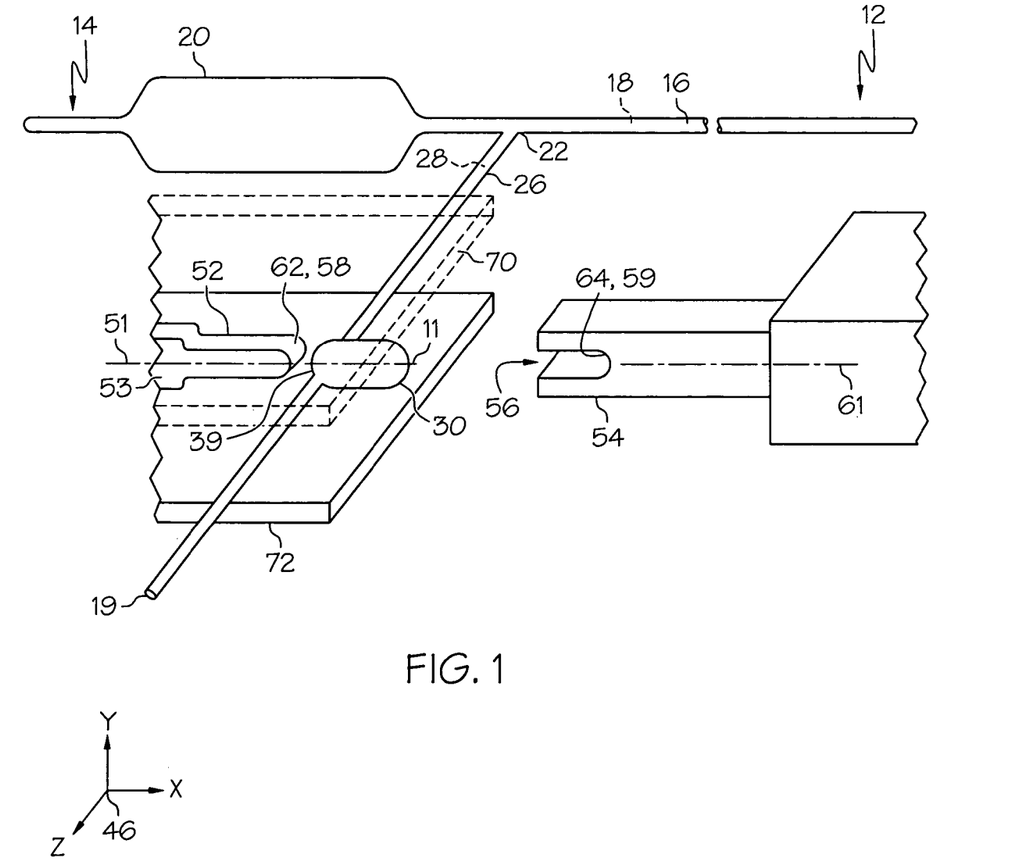
FIG. 1 shows an embodiment of a secondary balloon folding device.

FIG. 1 shows a balloon catheter 10 and an embodiment of a balloon folding device 50. The catheter 10 includes a primary inflation balloon 20 and a secondary inflation balloon 30. The folding device 50 is used to fold the secondary balloon 30 to a low profile configuration.

In various embodiments, the catheter 10 may be any catheter having a secondary inflation balloon 30 or similar inflatable portion, for example as disclosed in US Patent Application Publication 2005/0060027, the entire disclosure of which is hereby incorporated herein by reference in its entirety. Such catheters 10 are used for delivering and expanding stents designed to be deployed at a vessel bifurcation, which include dedicated side branch structure that unfolds into a side branch vessel. Examples of stents with unfoldable side branch structure are disclosed in US 2005/0060027 and U.S. patent application Ser. Nos. 11/138,202, 11/138,196 and 11/138,022, the entire disclosures of which are hereby incorporated herein by reference in their entireties.

The catheter 10 comprises an elongate shaft 16 having an internal lumen 18 extending therethrough. The shaft 16 has a proximal portion 12 and a distal portion 14. The primary inflation balloon 30 is located in proximity to the distal portion 14 of the shaft 16. An internal volume of the primary balloon 20 is in fluid communication with the internal lumen 18 of the shaft 16, thus allowing the primary balloon 30 to be inflated and deflated.

The secondary balloon 30 is attached to or formed integrally with a secondary shaft 26 having an internal lumen 28. An internal volume of the secondary balloon 30 is in fluid communication with the internal lumen 28. A proximal end of the secondary shaft 26 connects to the catheter shaft 16 at a proximal connection location 22. A distal end 19 of the secondary shaft 26 is sealed, thereby preventing an inflation medium from escaping or entering through the distal end 19 and allowing the secondary balloon 30 to be inflated and/or deflated while positioned within the folding device 50.

In some embodiments, the internal lumen 28 of the secondary shaft 26 is in fluid communication with the internal lumen 18 of the catheter shaft 16. Thus, the secondary balloon 30 may be arranged to inflatable and/or deflate simultaneously with the primary balloon 30. The connection between the two lumens 18, 28 may be made at the proximal connection location 22.

In some other embodiments, the secondary balloon 30 is arranged to be inflatable and deflatable independently from the primary balloon 20. In such embodiments, the catheter shaft 16 is provided with a second internal lumen that is in fluid communication with the secondary shaft lumen 28. A second internal lumen of the catheter shaft 16 may extend from the proximal connection location 22 to the proximal end 12 of the shaft 16.

FIG. 1 shows the catheter 10 positioned with the secondary balloon 30 extending away from the primary balloon 20 and oriented in the folding device 50. In some embodiments, after the secondary balloon 30 is folded, the secondary balloon 30 can be placed along side the primary balloon 20, and the distal end 19 of the secondary shaft 26 will be attached to the distal portion 14 of the catheter shaft 16.

The folding device 50 comprises a first die 52 and a second die 54, wherein at least one die 52, 54 is arranged to be moved with respect to the other. In some embodiments, the dies 52, 54 are removable and thus, various embodiments of dies 52, 54 may be interchanged as desired depending upon the balloon 30 being folded. In some embodiments, a central axis 51 of the first die 52 is oriented coaxially with a central axis 61 of the second die 54. In some embodiments, the first die 52 may remain fixed and the second die 54 is repositionable.

A die 52, 54 may be moved using any suitable method. In some embodiments, an actuation device, such as a pneumatic cylinder, is used to extend and retract a die 54. Movement of a die 54 is generally in a direction toward or away from the other die 52. In some embodiments, a die 54 is actuated along its central axis 54.

Each die 52, 54 includes a contacting surface 62, 64 that contacts a secondary balloon 30 during a folding operation. The contacting surfaces 62, 64 comprise complimentary shapes arranged to mate with one another while folding the balloon 30. The specific shape of each die 52, 54 will control the final folded shape of the balloon 30. In some embodiments, the dies 52, 54 are sized and positioned such that when the folding device 50 is in a fully closed configuration, an amount of space remains between the dies 52, 54 to allow for the thickness of the secondary balloon 30 material, and in some embodiments, to avoid pinching the secondary shaft 26.

Dies 52, 54 may be made of any suitable material and in various embodiments comprise metals, polymers, plastics, ceramics and/or various suitable combinations thereof. Various materials having different coefficients of friction may be used depending upon the specific fold configuration desired. For example, metals are suitable when it is desirable for the balloon to slide along a surface of a die 52, 54, while rubber is suitable when frictional engagement is desired. In some embodiments, a die 52, 54 can further comprise a coating to achieve a desired surface texture and/or frictional characteristics. In some embodiments, a die 52, 54 comprises an anodized coating. In some embodiments, a die 52, 54 comprises a low friction coating, such as a layer of PTFE.

Various embodiments of dies 52, 54 may have any suitable shape to impart a desired folded configuration to the balloon 30. In some embodiments, both contacting surfaces 62, 64 are be flat, and will thus fold the balloon 30 to a flat pancake shape. In some embodiments, the contacting surfaces 62, 64 comprise complimentary convex and concave dome shapes, and will thus fold the balloon 30 to a dome shape. The embodiment shown in FIG. 1 imparts a U-shape to a folded balloon 30, and thus the dies 52, 54 comprise complimentary U-shaped portions. An outer surface of the first die 52 comprises a U-shape having an external convex curved portion 58. Opposing sides 53 of the first die 52 are flat. The second die 54 comprises a cavity 56 having an internal concave curved portion 59.

FIG. 1 shows a coordinate axis 46 having an x-axis, a y-axis and a z-axis. A cross-sectional shape of either die 52, 54 taken in the xy plane includes curvature along the contacting surface 62, 64. A cross-sectional shape of either die 52, 54 depicted in FIG. 1, taken in the yz plane through the contacting surface 62, 64 of the die 52, 54 will generally comprise a rectangular shape. In various embodiments, the cross-sectional shape of the dies 52, 54 taken in the yz plane can have any suitable shape, such as round, square, rectangular, etc. Cross-sectional shapes taken in the yz plane that include flat sides and corners can help to control rotation of the balloon 30 during a folding operation.

During a secondary balloon 30 folding operation, the secondary balloon 30 is positioned adjacent to the first die 52 with a central axis 11 of the secondary balloon 30 oriented coaxially with the central axis 51 of the first die 52. A bottom side 39 of the secondary balloon 30 abuts the contacting surface 62 of the first die 52. In some embodiments, the catheter 10 is secured in place using any suitable method, and thus the secondary balloon 30 is prevented from moving along the z-axis via the secondary shaft 26. In some embodiments, the distal portion 19 of the secondary shaft 26 is held by an operator or otherwise braced against movement.

In some embodiments, the folding device 50 further comprises an upper guard 70 and a lower guard 72 to prevent the secondary balloon 30 from displacing along the y-axis.

In some embodiments, the secondary balloon 30 is inflated to its full inflated size and shape, for example by using an inflation fluid. In some embodiments, the secondary balloon 30 folding operation is conducted simultaneously with a primary balloon 20 folding operation. Thus, the folding device 50 is located in proximity to a primary balloon folding device and oriented such that both balloons 20, 30 are in their respective folding devices simultaneously. This can be done, for example, when the primary balloon 20 and the secondary balloon 30 are in fluid communication with one another and thus inflate and deflate simultaneously.

The second die 54 is actuated in the direction of the secondary balloon 30. As the second die 54 contacts the balloon 30, it begins to reduce the size of the balloon 30, thereby forcing inflation fluid out of the balloon 30 and folding the balloon 30 to a predetermined folded shape.

Figure 2:
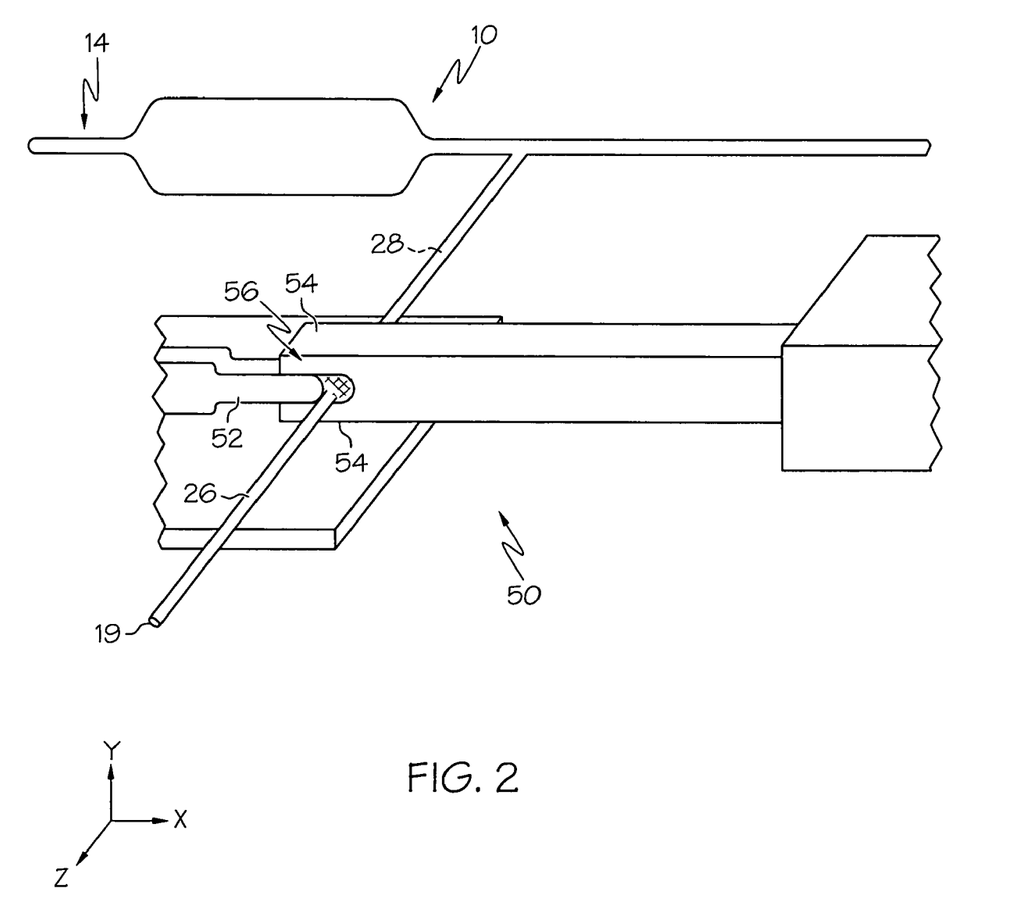
FIG. 2 shows an embodiment of a folding device performing a folding operation.

FIG. 2 shows the folding device 50 having the second die 54 near the end of its travel and displaced to the extent that a portion of the first die 52 extends into the cavity 56 of the second die 54. The entire secondary balloon 30 is oriented within the cavity 56 and has been folded by compression along its central axis 11. Folding operations that force the balloon 30 to be reduced in the axial 11 direction impart folds that encourage the balloon 30 to later inflate in the axial 11 direction, which is desirable for proper expansion of the aforementioned stent side branch structure.

In some embodiments, the dies 52, 54 are constructed and arranged such that the folding operation will not pinch the secondary shaft 26. In some embodiments, travel of the dies 52, 54 is limited accordingly. In some embodiments, the dies 52, 54 are shaped to account for the secondary shaft 26. For example, the width of first die 52 along the z-axis may be less than the distance across the balloon 30 between attachment points to the secondary shaft 26. In some embodiments, one or both of the dies 52, 54 include nesting grooves that receive the secondary shaft 26 during the folding operation.

When the secondary balloon 30 is fully compressed, vacuum is introduced to the inflation lumen 28 to ensure the balloon 30 remains in the folded configuration. The secondary balloon 30 is then positioned adjacent to the primary balloon 20, which generally will have also been deflated and folded. In some embodiments, the distal end 19 of the secondary shaft 26 is attached to the distal end 14 of the catheter 10. The two balloons 20, 30 may then be formed together in an iris mechanism to achieve the final cumulative folded profile.

Figure 3:
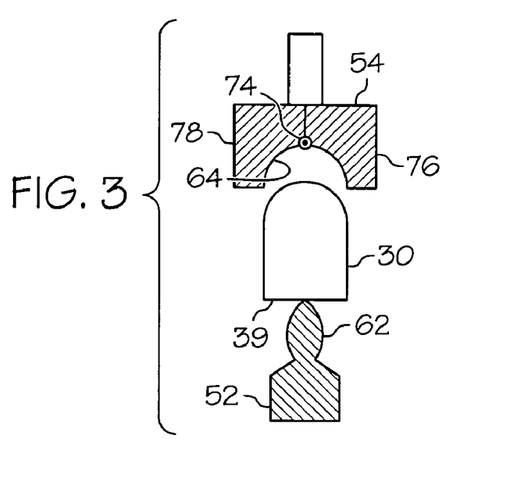
FIGS. 3-5 show an embodiment of a folding device performing a folding operation.
Figure 4:
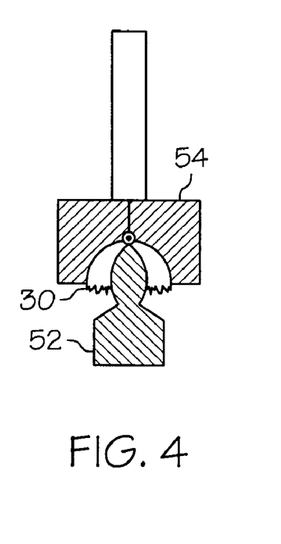
Figure 5:
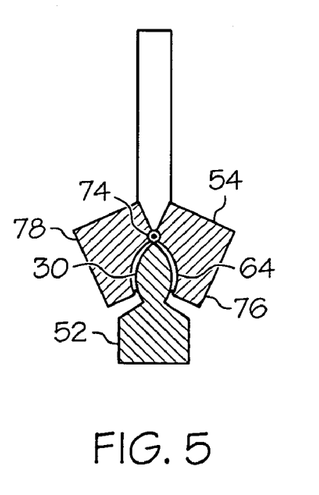

FIGS. 3-5 illustrate a balloon folding operation using further embodiments of dies 52, 54. The second die 54 comprises a first portion 76 and a second portion 78 arranged to move with respect to one another. The specific embodiment of FIGS. 3-5 comprises a hinge 74. Operation of the hinge 74 causes the contacting surfaces 64 of each portion 76, 78 to move closer to one another. FIG. 3 shows the second die 54 in a first, open configuration, and FIG. 5 shows the second die 54 in a second, closed configuration. The first die 52 is shaped such that the contacting surface 62 compliments the second die 54 when the second die 54 is in the second or closed configuration.

During a folding operation, the secondary balloon 30 is placed between the dies 52, 54 and inflated. The second die 54 is moved toward the balloon 30 and the first die 54.

FIG. 4 shows the second die 54 at the end of its travel in the direction of the first die 52. The balloon 30 has been reduced along its axial direction.

As shown in FIG. 5, the first portion 76 and the second portion 78 are then pivoted about the hinge 74 to move the contacting surfaces 64 of the second die 54 toward one another. This further reduces the balloon 30 in profile and shapes the balloon 30.

In alternative embodiments, the first die 52 is provided with multiple portions and constructed such that the contacting surfaces 62 are able to move away from one another. In some embodiments, one die 52 includes multiple portions and a hinged connection while the other die 54 travels in the axial direction.

Figure 6:
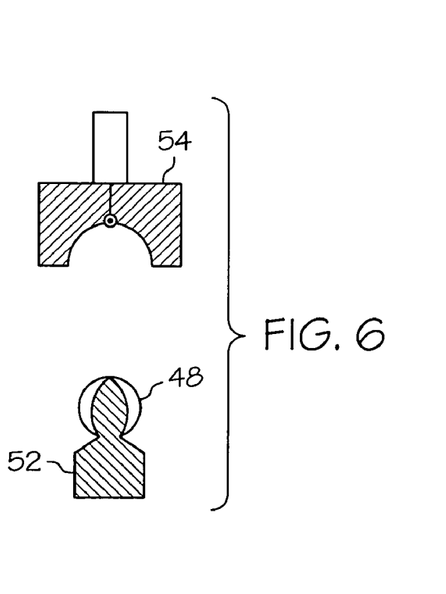
FIG. 6 shows embodiments of dies that may be used in the folding device.

FIG. 6 shows further embodiments of dies 52, 54. In some embodiments, one or both of the dies 52, 54 are provided with one or more inflatable bladders 48. Each bladder 48 is inflated and deflated as desired during a folding operation. An air bladder 48 may be used as a substitute for a die having multiple hinged portions 76, 78 (see FIG. 5) to achieve a similar result.

Figure 7:
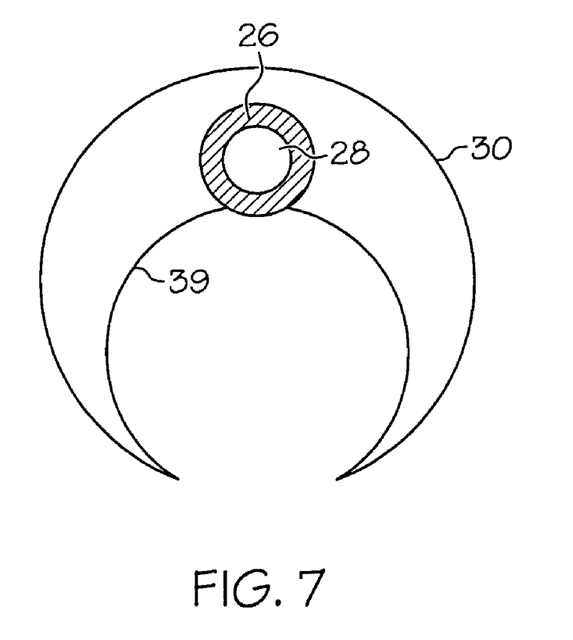
FIG. 7 shows an embodiment of a folded secondary balloon.

FIG. 7 shows a view of a folded secondary balloon 30 taken in an axial direction of the secondary shaft 26. This view would be similar to looking down the z-axis shown in FIG. 1. The balloon 30 has been folded by an embodiment of a folding device 50 designed to impart a folded crescent shape, for example as shown in FIGS. 3-5. The bottom portion 39 (see FIG. 1 or 3) of the secondary balloon 30 comprises an inner surface of the crescent shape.

Figure 8:
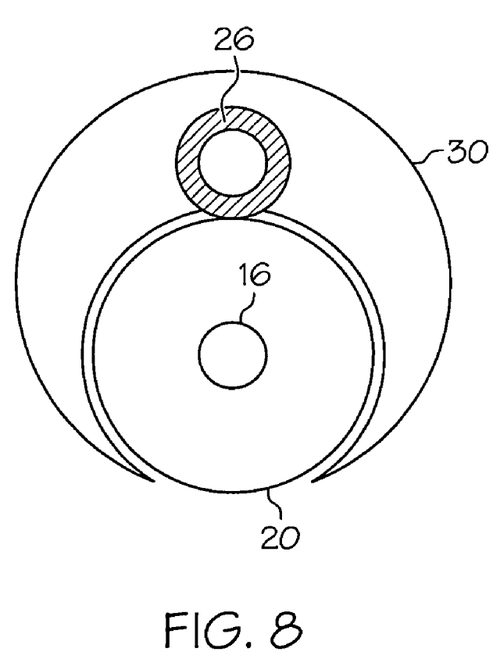
FIG. 8 shows the balloon of FIG. 7 oriented about a primary balloon.

FIG. 8 shows a secondary balloon 30 folded into a crescent configuration and oriented about a folded primary balloon 20. The folded crescent configuration of the secondary balloon 30 is particularly suitable for making a balloon catheter 10 with a low profile.

Figure 9:
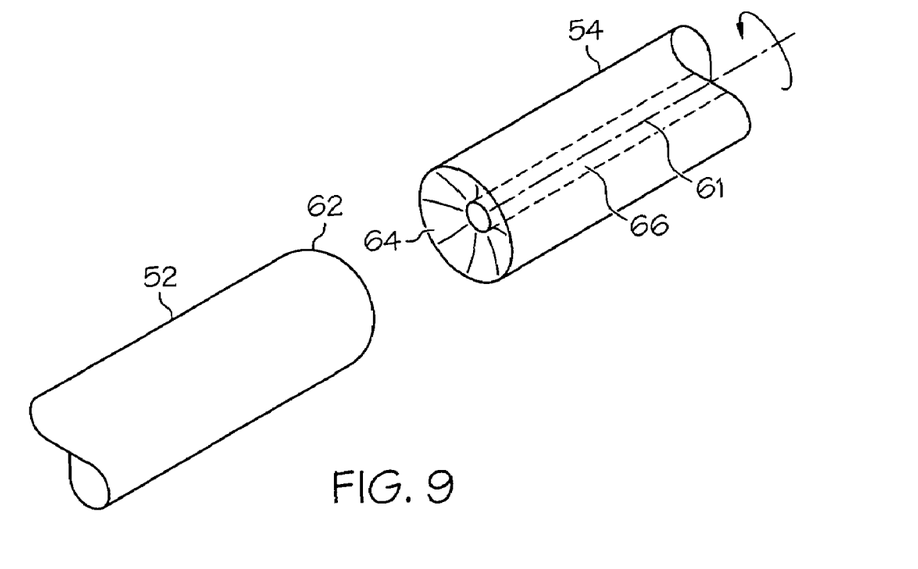
FIG. 9 shows embodiments of dies that may be used in the folding device.

FIG. 9 shows further embodiments of dies 52, 54. The contacting surface 62 of the first die 52 comprises a convex dome shape. The contacting surface 64 of the second die 54 comprises a concave dome shape having three-dimensional curvature that is complimentary to the contacting surface 62 of the first die 52.

Figure 10:
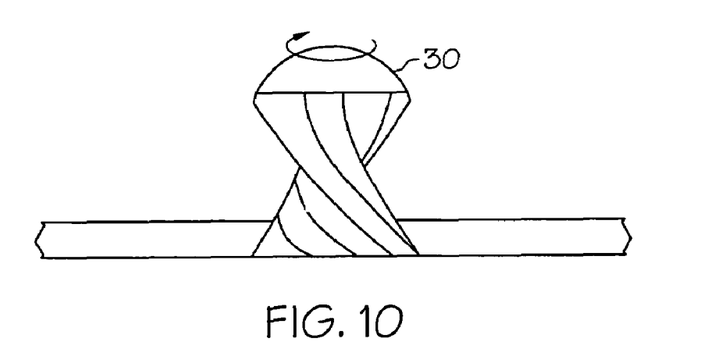
FIGS. 10 and 11 show a secondary balloon as folded with an embodiment of a secondary balloon folding device.
Figure 11:
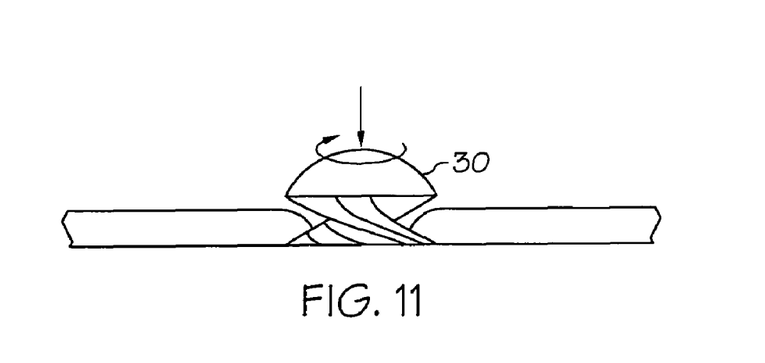

In some embodiments, at least one of the dies 52, 54 is rotatable. In the embodiment of FIG. 9, the second die 54 is rotatable about its central axis 61. Thus, in some embodiments, a folding device 50 is capable of imparting the balloon 30 with a rotational fold, wherein the die 54 rotates as it contacts and folds the balloon 30. A balloon 30 having a rotational fold is illustrated in FIGS. 10 and 11.

Again referring to FIG. 9, the second die 54 further comprises an internal lumen 66 that extends to the contacting surface 64. The lumen 66 is used, for example, to apply a vacuum, thereby engaging and holding the balloon 30 against the contacting surface 64 during a folding operation. In some embodiments, a balloon 30 is inflated and positioned between the dies 52, 54. The dies 52, 54 are moved such that the contacting surface 51, 61 of each die 52, 54 contacts the balloon 30. Vacuum is applied to the lumen 66 of the second die 54, thereby engaging the balloon 30 and preventing it from moving away from the second die 54. In some embodiments, prior to further axial movement of the second die 54, the die 54 is rotated, causing rotation of one end of the balloon 30, for example as shown in FIG. 10. This reduces the interior volume of the balloon 30 and expels a portion of the inflation fluid. The second die 54 is then displaced axially in the direction of the balloon 30, and in some embodiments further rotated to complete the fold, for example as shown in FIG. 11.

In some embodiments, the dies 52, 54 are made from rubber or another material having a coefficient of friction suitable to frictionally engage the balloon 30.

In some embodiments, a portion of a die 52, 54, such as the contacting surface 62, 64, is coated or otherwise treated to increase its ability to temporarily engage the balloon 30. For example, a die 52, 54 may be coated with rubber or another material having a high coefficient of friction. In some embodiments, a die 52, 54 is coated with a releasable adhesive, such as a microsphere adhesive which limits the amount of surface area contact between the adhesive and the balloon 30. A releasable adhesive engages the balloon 30 as the die 52, 54 contacts the balloon 30 and releases the balloon 30 as the dies 52, 54 are retracted. In some embodiments, a texturized surface may be imparted to the die 52, 54, for example by applying a textured or granular coating, or by machining the surface 62, 64 of the die 52, 54 to create pits and/or grooves.

A balloon 30 with a rotational fold, for example as shown in FIG. 11, is particularly suitable for expanding stents with side branch structure that is designed to rotate about the center of the side branch area during expansion, the entire disclosure of which is hereby incorporated be reference in its entirety.

Figure 12:
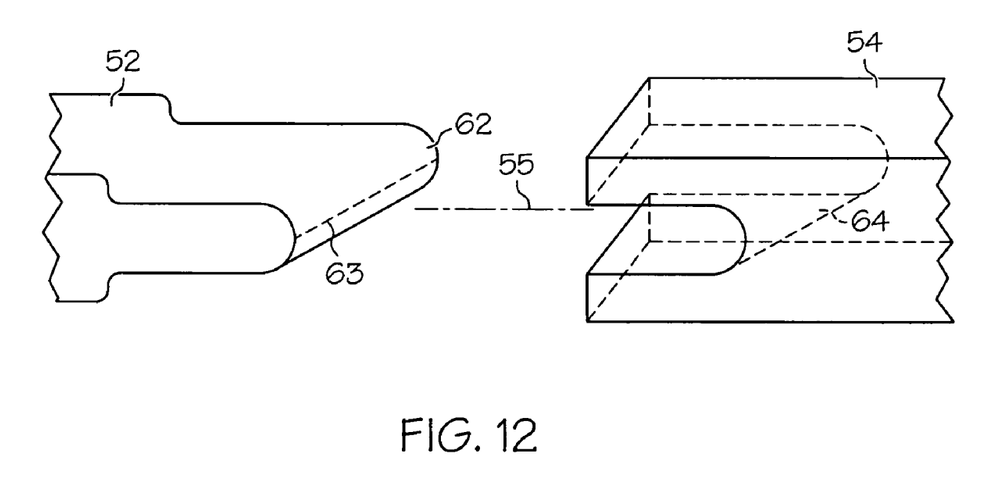
FIG. 12 shows embodiments of dies that may be used in the folding device.

FIG. 12 shows further embodiments of dies 52, 54 having a contacting surface 62, 64 oriented at a nonperpendicular angle to the actuation axis 55 of a moving die 54. In some embodiments, a portion (for example as illustrated by line 63) of a contacting surface 62, 64 is straight along its length and oriented at a nonperpendicular angle to the actuation axis 55. Such embodiments are particularly suitable for folding balloons 30 that have a central axis 11 oriented nonperpendicular to the secondary shaft 26 (see FIG. 1).

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to."

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A balloon folding device for folding a secondary balloon of a bifurcation balloon catheter comprising a primary balloon and said secondary balloon, said secondary balloon suitable for unfolding a side branch structure of a bifurcation stent, said balloon folding device comprising:
    a first die having an external contacting surface; and
    a second die comprising a first portion moveable with respect to a second portion, the second die having a cavity, a portion of the cavity comprising a contacting surface, the contacting surface comprising a first contacting section and a second contacting section, the first portion comprising the first contacting section and the second portion comprising the second contacting section;
    wherein the second die is movable with respect to the first die along a linear path during a first portion of a balloon folding procedure, and during movement the external contacting surface of the first die moves within the cavity of the second die, the contacting surfaces constructed and arranged to contact the secondary balloon.

2. The balloon folding device of claim 1, wherein the cavity of the second die comprises first and second opposed sides connected by said contacting surface.

3. The balloon folding device of claim 1, wherein the external contacting surface of the first die is shaped complimentary to the contacting surface of the second die.

4. The balloon folding device of claim 1, wherein the external contacting surface of the first die comprises an end of the first die.

5. The balloon folding device of claim 1, wherein the contacting surface of the first die comprises an external convex surface.

6. The balloon folding device of claim 1, wherein the contacting surface of the second die comprises an internal concave surface.

7. The balloon folding device of claim 1, wherein the first contacting section moves toward the second contacting section during a second portion of said balloon folding procedure.

8. The balloon folding device of claim 1, wherein the first portion and the second connection are connected by a hinge.

9. The balloon folding device of claim 1, the second die having an open configuration and a closed configuration, wherein a distance between the first contacting section and the second contacting section is less when the die is in the closed configuration.

10. The balloon folding device of claim 9, wherein the external contacting surface of the first die is shaped complimentary to the contacting surface of the second die when the second die is in the closed configuration.

11. The balloon folding device of claim 1, wherein the contacting surface of at least one die further comprises an inflatable bladder.

12. The balloon folding device of claim 1, wherein the contacting surface of at least one die comprises a U-shape.

13. A balloon folding device for folding a secondary balloon of a bifurcation balloon catheter comprising a primary balloon and said secondary balloon, said secondary balloon suitable for unfolding a side branch structure of a bifurcation stent, said balloon folding device comprising:
    a first die having an external contacting surface; and
    a second die having a cavity, a portion of the cavity comprising a contacting surface;
    wherein the second die is movable with respect to the first die, and during movement the external contacting surface of the first die moves within the cavity of the second die, the contacting surfaces constructed and arranged to contact the secondary balloon;
    the second die further comprising an internal lumen that extends to the contacting surface.

14. The balloon folding device of claim 1, wherein the second die is rotatable about its central axis.

15. The balloon folding device of claim 13, wherein the contacting surface of at least one die comprises a dome.

16. The balloon folding device of claim 1, wherein the contacting surface of at least one die is oriented at a nonperpendicular angle to an actuation axis of the moving die.

17. The balloon folding device of claim 1, further comprising an actuation device for moving the second die with respect to the first die.

18. The balloon folding device of claim 13, further comprising a vacuum source in fluid communication with said internal lumen.

19. The balloon folding device of claim 1, wherein said folding device compresses the balloon to form a crescent shape.

20. The balloon folding device of claim 13, wherein said second die rotates with respect to said first die during said movement.

* * * * *